US00PP27250P3

(12) United States Plant Patent
Renault

(10) Patent No.: US PP27,250 P3
(45) Date of Patent: Oct. 11, 2016

(54) ***EUCALYPTUS* PLANT NAMED 'RENGUN'**

(50) Latin Name: *Eucalyptus gunnii*
Varietal Denomination: Rengun

(71) Applicant: Jean Renault, Gorron (FR)

(72) Inventor: Jean Renault, Gorron (FR)

( * ) Notice: Subject to any disclaimer, the term of this patent is extended or adjusted under 35 U.S.C. 154(b) by 115 days.

(21) Appl. No.: 14/544,080

(22) Filed: Nov. 24, 2014

(65) Prior Publication Data

US 2016/0150704 P1 May 26, 2016

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Susan McCormick Ewoldt
(74) *Attorney, Agent, or Firm* — Cassandra Bright

(57) ABSTRACT

A new and distinct *Eucalyptus* cultivar named 'Rengun' is disclosed, characterized by distinctive small, Grey-Green foliage. Plants have a distinctive bushy growth habit, form small to medium sized shrubby trees. The new cultivar is a *Eucalyptus*, suitable for ornamental garden purposes.

3 Drawing Sheets

Latin name of the genus and species: *Eucalyptus gunnii.*
Variety denomination: 'Rengun'.

BACKGROUND OF THE INVENTION

The new cultivar is a product of chance discovery by the inventor. This new variety, hereinafter referred to as 'Rengun', was discovered as a naturally occurring, whole plant mutation by the inventor, Jean Renault. The interesting new mutation was discovered in a commercial nursery in Gorron, France among a population of unpatented *Eucalyptus gunnii* during April of 2009.

After identifying the new variety as a potentially interesting selection, the inventor first organized propagation of 'Rengun' by vegetative cuttings at the same commercial nursery during May of 2011. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'Rengun' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Rengun' These characteristics in combination distinguish 'Rengun' as a new and distinct *Eucalyptus* cultivar:

1. Unique small foliage:
2. Dense, bushy growth.
3. Small to moderately sized shrubby tree.
4. Grey-Green leaf color.

COMPARISON TO PARENT VARIETY

'Rengun' is similar in most horticultural characteristics to the parent variety *Eucalyptus gunnii.* Plants of the new cultivar 'Rengun' however, differ in the following:

1. Plants of the new variety grow more slowly.
2. Plants of the new variety have smaller leaves.
3. Plants of the new variety are shorter.
4. Plants of the parent variety are more upright and less bushy than the new variety.

COMMERCIAL COMPARISON

'Rengun' is similar in most horticultural characteristics to the commercial variety *Eucalyptus gunnii* 'Azura', unpatented. Plants of the new cultivar 'Rengun' however, differ in the following:

1. Plants of the new variety are significantly shorter than plants of 'Azura'.
2. Plants of the new variety have much smaller leaves.
3. Plants of the new variety produce foliage with a different shape.
4. Plants of new variety produce foliage of a less blue coloration.

BRIEF DESCRIPTION OF THE PHOTOGRAPHS

The accompanying photograph in FIG. 1 illustrates in full color three typical plants of 'Rengun' grown outdoors in Angers, France. The plants are approximately 1.5 years old, and is shown growing in approximately 2 liter containers.

Figure 1:
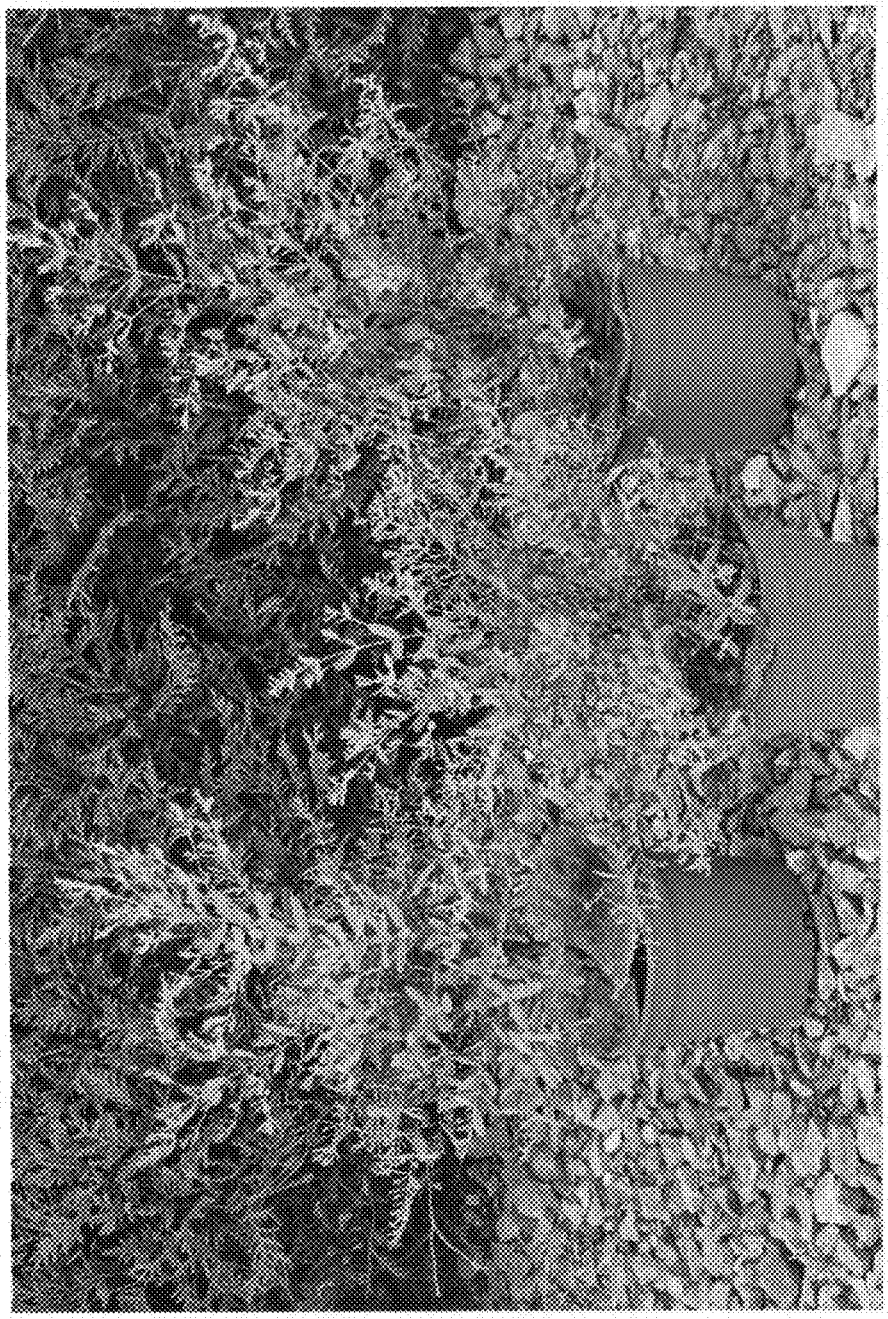
Figure 2:
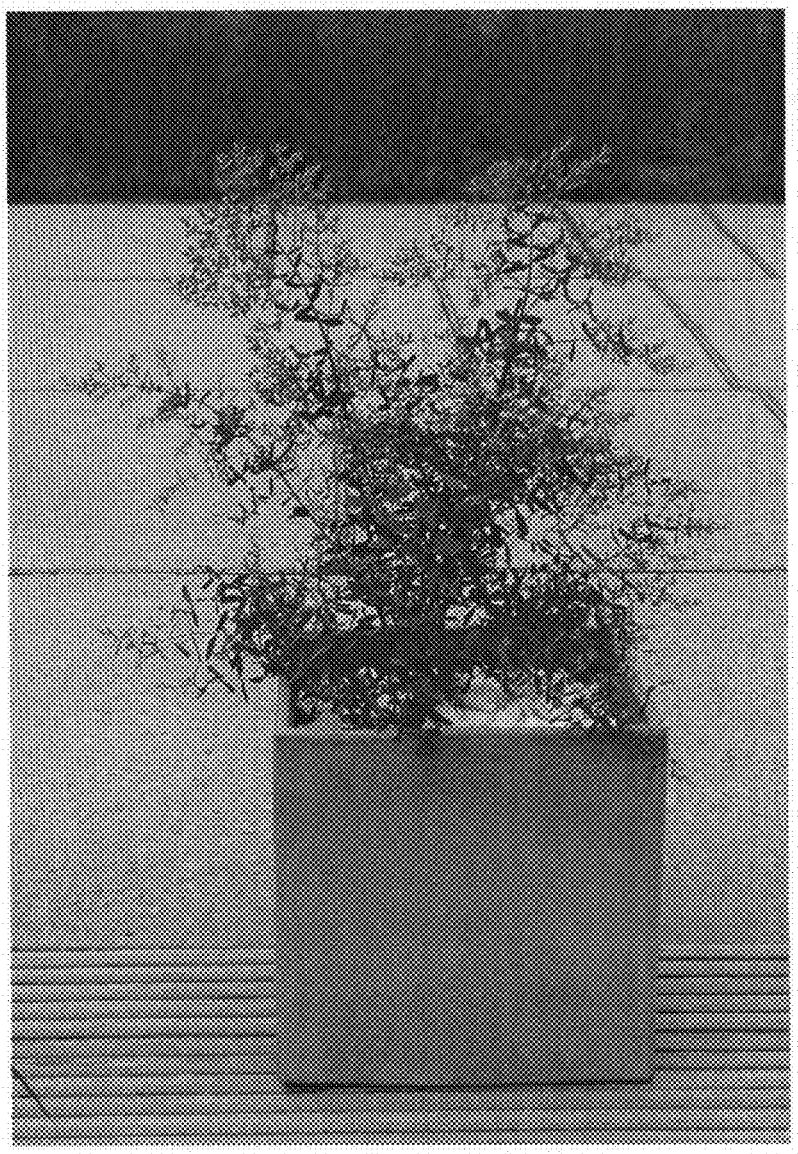
FIG. 2 illustrates a single plant, of approximately 2.5 years.
Figure 3:
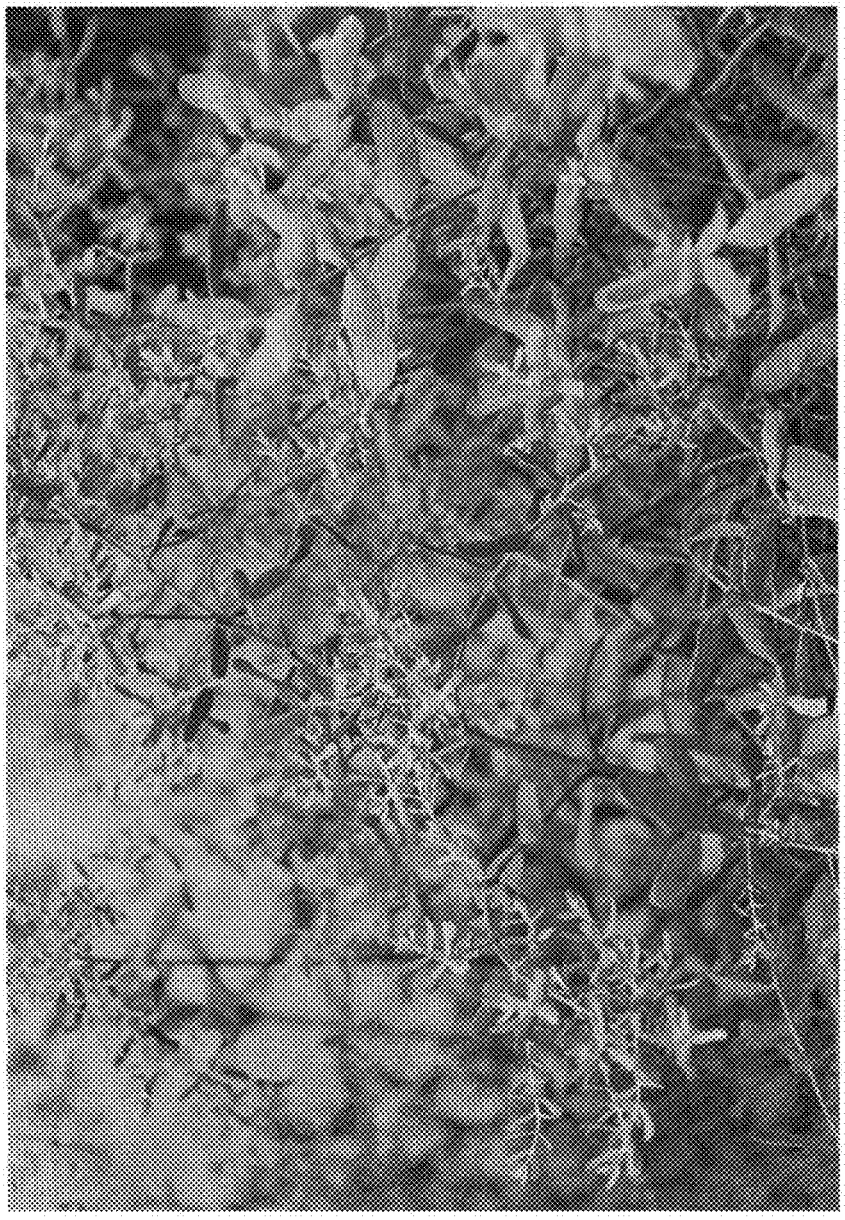
FIG. 3 shows a close up of typical foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Rengun' plants grown outdoors in Angers, France. Plants are approximately 3 years old, in a 5 liter nursery container. Measurements and numerical values represent averages of typical plant types.

Botanical classification: *Eucalyptus gunnii* 'Rengun'.

PROPAGATION

Time to produce a rooted cutting: Approximately 150 days at approximately 18° C.

Root description: Fibrous, very well branched. Colored near RHS Brown N200C.

Typical propagation method: Tissue culture or softwood cuttings.

PLANT

Growth habit: Upright, well branched shrubby tree.

Height: 1 meter.

Plant spread: 0.70 m.

Overall plant shape: Loosely globular, bushy, especially near base.

Growth rate: Moderate.

Trunk color: Grey-Brown 199 A.

Trunk diameter: Average 2 cm.

Trunk texture: Smooth.

Internode length: Approximately 2.5 cm.

Branching characteristics:

*Diameter of lateral branches.*—Approximately 0.4 cm for primary branches (after pinching). Approximately 0.1 cm for secondary branching (unpinched growth).

*Quantity of lateral branches.*—Approximately 10 primary branches.

*Texture of lateral branches.*—Smooth.

*Color of lateral branches.*—Near RHS Yellow-Green 144C.

*Aspect and angle.*—Straight primary branches, occurring at approximately 55° angle, from base, secondary branches occur at wide angles, approximately 90 to 135 degrees from primary stems.

*Strength of lateral branches.*—Rigid and woody at base, soft and flexible further along branches.

*Internode length.*—Approximately 2.5 cm.

FOLIAGE

Leaf:

*Arrangement.*—Opposite.

*Average length.*—Approximately 2 cm.

*Average width.*—Approximately 0.9 cm.

*Shape of blade.*—Somewhat irregular elliptic.

*Apex.*—Rounded.

*Base.*—Blunt.

*Attachment.*—Sessile.

*Margin.*—Entire.

*Texture of top surface.*—Non pubescent, somewhat foveate.

*Texture of bottom surface.*—Glabrous.

*Leaf internode length.*—Average range 0.5 cm to 1.2 cm.

*Color.*—Young foliage upper side: Near RHS Green N138C, overlay coloration Greyed-Green 188C. Young foliage under side: Near RHS Green N138C, overlay coloration Greyed-Green 188B. Mature foliage upper side: Near RHS Green N138C, overlay coloration Greyed-Green 190B. Mature foliage under side: Near Green RHS N138C, overlay coloration Greyed-Green 190B.

*Venation.*—Type: Pinnate. Venation color: Indistinguishable from foliage color.

FLOWER

Flowering not observed to date.

OTHER CHARACTERISTICS

Disease and pest resistance: Neither resistance nor susceptibility observed.

Drought tolerance: Moderate tolerance for drought, requires at least minimum Summer watering.

Temperature tolerance: Tolerates low temperatures to at least −10° C., high temperature tolerance to at least 40° C.

What is claimed is:

1. A new and distinct cultivar of *Eucalyptus* plant named 'Rengun' as herein illustrated and described.

* * * * *